United States Patent
Doi et al.

(10) Patent No.: US 7,769,216 B2
(45) Date of Patent: Aug. 3, 2010

(54) FACILITATING COMPARISON OF MEDICAL IMAGES

(75) Inventors: Takeshi Doi, Cupertino, CA (US); Vilim Simcic, Los Gatos, CA (US); Jimmy R. Roehrig, Aptos, CA (US)

(73) Assignee: Hologic, Inc., Marlborough, MA (US)

( * ) Notice: Subject to any disclaimer, the term of this patent is extended or adjusted under 35 U.S.C. 154(b) by 1219 days.

(21) Appl. No.: 11/323,939

(22) Filed: Dec. 29, 2005

(65) Prior Publication Data

US 2007/0160271 A1    Jul. 12, 2007

(51) Int. Cl.
*G06K 9/00* (2006.01)
(52) U.S. Cl. .......................................... 382/128; 378/4
(58) Field of Classification Search ................ 382/100, 382/128, 130, 131, 294; 128/922; 378/4–27
See application file for complete search history.

(56) References Cited

U.S. PATENT DOCUMENTS

| | | | |
|---|---|---|---|
| 5,359,513 A | 10/1994 | Kano et al. | |
| 5,982,915 A | 11/1999 | Doi et al. | |
| 6,067,373 A | 5/2000 | Ishida et al. | |
| 6,317,617 B1 | 11/2001 | Gilhuijs et al. | |
| 6,594,378 B1 | 7/2003 | Li et al. | |
| 6,771,736 B2 | 8/2004 | Sabol et al. | |
| 6,909,792 B1 | 6/2005 | Carrott et al. | |
| 7,103,205 B2* | 9/2006 | Wang et al. | 382/132 |
| 7,313,260 B2* | 12/2007 | Wang et al. | 382/128 |
| 7,542,791 B2* | 6/2009 | Mire et al. | 600/407 |
| 2002/0082484 A1 | 6/2002 | Baba et al. | |
| 2002/0090126 A1 | 7/2002 | Oosawa | |
| 2004/0017935 A1 | 1/2004 | Avinash et al. | |
| 2004/0022425 A1 | 2/2004 | Avinash et al. | |
| 2004/0068170 A1* | 4/2004 | Wang et al. | 600/407 |
| 2004/0081342 A1 | 4/2004 | Sato | |
| 2004/0114790 A1 | 6/2004 | Yamamoto et al. | |
| 2004/0122704 A1 | 6/2004 | Sabol et al. | |
| 2004/0122787 A1 | 6/2004 | Avinash et al. | |
| 2004/0252873 A1 | 12/2004 | Avinash et al. | |
| 2005/0084178 A1 | 4/2005 | Lure et al. | |
| 2005/0111718 A1 | 5/2005 | MacMahon et al. | |
| 2005/0111720 A1 | 5/2005 | Gurcan et al. | |
| 2005/0113961 A1 | 5/2005 | Sabol et al. | |
| 2005/0163360 A1 | 7/2005 | Snoeren et al. | |

* cited by examiner

*Primary Examiner*—Anand Bhatnagar
(74) *Attorney, Agent, or Firm*—Brian J. Daiuto

(57) ABSTRACT

Facilitating viewer comparison of a plurality of medical images of at least one body part on a softcopy review workstation is described. First and second medical images are displayed such that the second medical image appears as a spatially registered underlay to the first medical image exposed through an aperture therein. The aperture comprises at least one edge that is viewer-manipulable in a back-and-forth manner so that the first and second medical images can be visually compared with minimal eye movement. For a temporal comparison embodiment, the first and second medical images comprise identical views of the same body part acquired at different times. For a cross-modality comparison embodiment, the first and second medical images are acquired substantially concurrently, or at different times, using different medical imaging modalities. For a bilateral comparison embodiment, the first and second images are corresponding views of two laterally corresponding body parts.

23 Claims, 5 Drawing Sheets

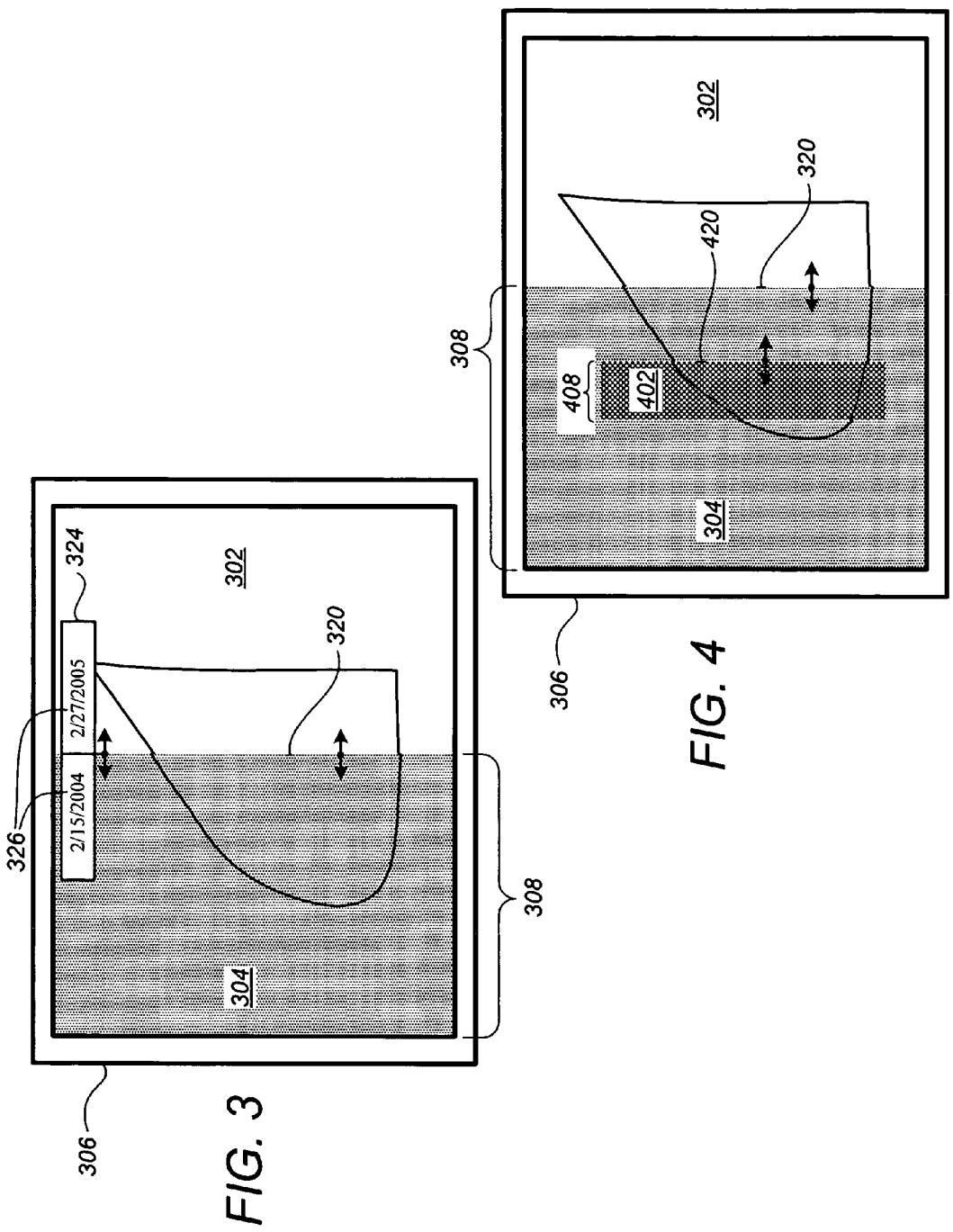

FACILITATING COMPARISON OF MEDICAL IMAGES

FIELD

This patent specification relates to medical imaging. More particularly, this patent specification relates to facilitating viewer comparison of medical images.

BACKGROUND

An ongoing tension is found in today's radiology environment between providing high-quality image review and maintaining adequate patient throughput to keep costs under control. Despite ongoing advances in imaging technology and related data processing systems, it is the radiologist who continues to bear the burden of the cost-quality tradeoff. As used herein, radiologist generically refers to a medical professional that analyzes medical images and makes clinical determinations therefrom, it being understood that such person might be titled differently, or might have differing qualifications, depending on the country or locality of their particular medical environment.

With the best of intentions, the medical imaging equipment industry continues to develop more technology to provide more image information and/or more decision support information to the radiologist for detecting and/or diagnosing a particular condition. However, this additional information can sometimes frustrate the radiologist, already pressured by workload and cost considerations, by adding another layer of complexity to the process, and/or by presenting the additional information in awkward or non-intuitive user interfaces.

Even subtle user interface issues associated with image presentation tools and/or decision support tools can have a significant impact on the radiologist review rate and/or the quality of detection/diagnosis. One such user interface issue relates to user comparison of two or more medical images of at least one body part as may arise in the context of temporal comparison (e.g., comparison of two images of the same body part taken at different times), cross-modality comparison (e.g., comparison of two images of the same body part acquired with different imaging modalities), bilateral comparison (e.g., comparison of two laterally corresponding body parts, such as the left breast and right breast or the left lung and right lung), and in other contexts.

Some proposals have been made in relation to user comparison of medical images, such as those discussed in U.S. 2004/0122787 A1, which is incorporated by reference herein. In one such proposal, the two medical images are simply placed side-by-side on a display monitor, e.g., the first medical image is on the left-hand side of the monitor and the second medical image is on the right-hand side of the monitor. In other proposals, various predetermined pixelwise algorithms are performed on the first and second medical images to produce a third image, and the third image is displayed. Examples include difference imaging and a so-called enhanced division method that is discussed in U.S. 2004/0122787 A1, supra, in which the pixels of the third image are set equal to $[I1*I2]/[I1*I2+\Phi]$, where I1 and I2 are the first and second images, respectively, and $\Phi$ is a scalar constant greater than zero. In still other proposals, so-called fusion images are displayed that are yielded by running computer-aided detection (CAD) algorithms or other automated algorithms on the first and second medical images to detect changes therebetween, and then synthetically highlighting changed locations on a display of the first or second medical image. For each of the above proposals, the first and second images can initially be placed into spatial registration using affine image transformation, image warping, or other known methods.

However, each of the above proposals brings about one or more shortcomings that are at least partially addressed by one or more of the preferred embodiments herein. For example, side-by-side placement brings about the need for substantial eye movement between a region of interest on the first medical image and a corresponding region of interest in the second medical image, which can lead to radiologist fatigue in higher-volume environments, or which may be undesirable for other reasons. As another example, when viewing a difference image, enhanced division image, or fused image, the radiologist is no longer perceiving an "original" or "diagnostic-quality" looking image, but rather is perceiving a synthesized grayscale and/or colorized result. Although not intrinsically problematic, it can be argued that many radiologists might prefer to stay with images that are closer in nature to the "original" or "diagnostic-quality" medical images with which they are more comfortable, and for which they are accountable, when detecting and/or assessing image changes. At the same time, however, it would be desirable to avoid the substantial eye movement implicated by general side-to-side placement of the two images.

SUMMARY

A system, method, and related computer program products are provided for facilitating viewer comparison of a plurality of medical images of at least one body part on a softcopy review workstation. First and second medical images are displayed such that the second medical image appears as a spatially registered underlay to the first medical image exposed through a first aperture therein. The first aperture comprises at least one edge that is viewer-manipulable in a back-and-forth manner so that the first and second medical images can be visually compared with minimal eye movement.

In one preferred embodiment, a third medical image is also displayed such that the third medical image appears as a spatially registered underlay to the second medical image exposed through a second aperture therein when the second aperture is at least partially viewable through the first aperture in the first medical image. The second aperture also comprises at least one edge that is viewer-manipulable in a back-and-forth manner so that the first, second, and third medical images can be visually compared with minimal eye movement.

Although particularly useful in the context of temporal comparison of x-ray mammograms, the preferred embodiments can be advantageously used for a variety of medical image comparison scenarios. For example, the medical images being compared can be identical views of any body part (e.g., chest, abdomen, head, neck, etc.) acquired at different times using the same medical imaging modality such as, but not limited to, x-ray, ultrasound, computerized tomography (CT), magnetic resonance imaging (MRI), positron emission tomography (PET), and single-photon emission computed tomography (SPECT). As another example, the medical images can be corresponding views of two laterally corresponding body parts, such as the left breast and right breast or the left lung and right lung (in such case the spatial registration includes lateral flipping of one of the images). As another example, the medical images can be from different ones of the above medical imaging modalities acquired at the same time or at different times. As still another example, the medical images being compared can comprise nearby parallel planes of a three dimensional data volume. As yet another example, the medical images being compared can comprise nearby parallel planes of a quasi-three dimensional volume such as an x-ray tomosynthesis result set.

BRIEF DESCRIPTION OF THE DRAWINGS

FIG. 3 illustrates a review workstation display facilitating comparison of two medical images according to a preferred embodiment;

FIG. 4 illustrates a review workstation display facilitating comparison of three medical images according to a preferred embodiment;

DETAILED DESCRIPTION

Figure 1:
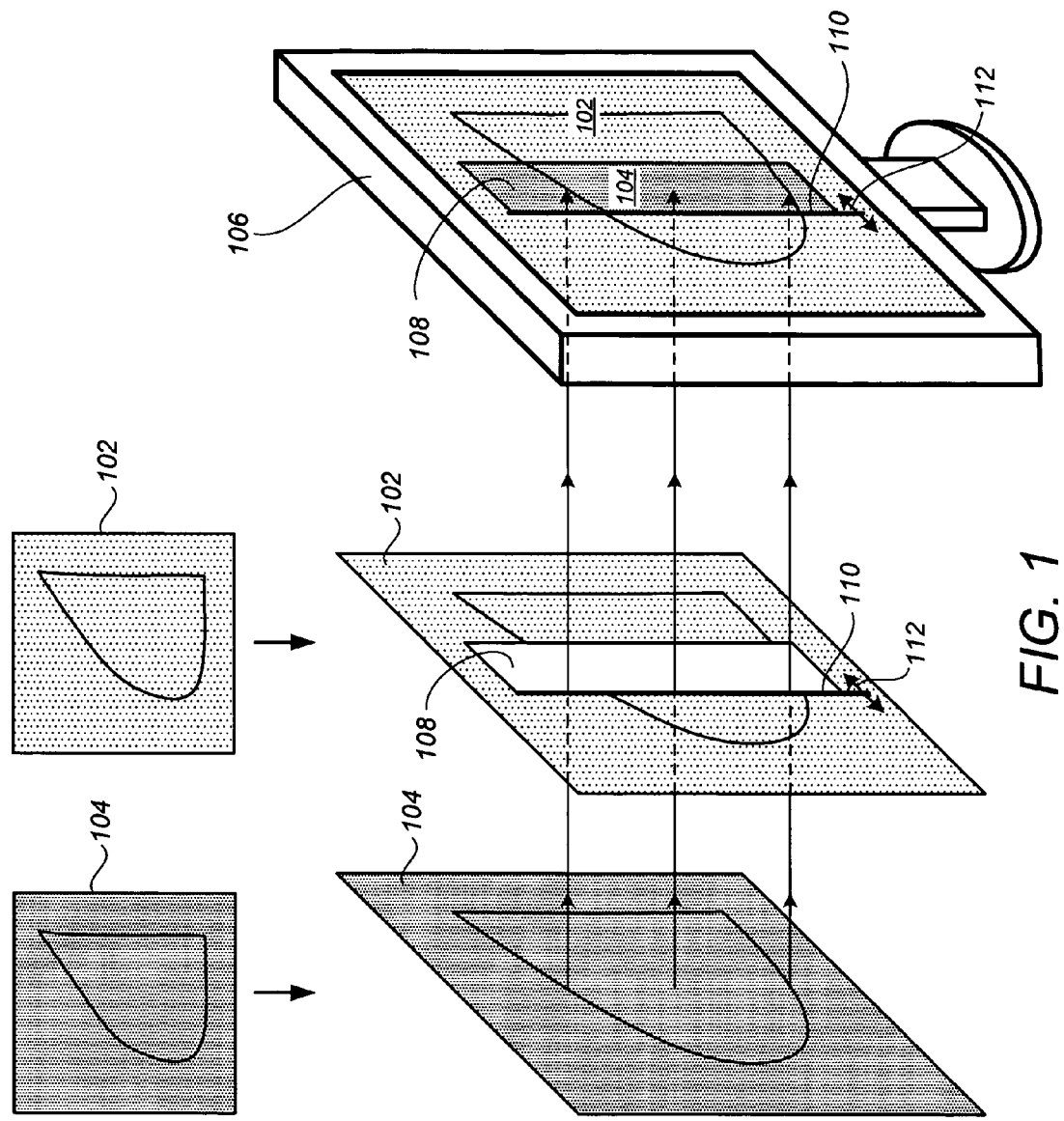
FIG. 1 illustrates a conceptual diagram of displaying first and second medical images in a manner that facilitates comparison thereof according to a preferred embodiment.

FIG. 1 illustrates a conceptual diagram of displaying a first medical image 102 and a second medical image 104 in a manner that facilitates comparison thereof according to a preferred embodiment. In the particular preferred embodiment of FIG. 1, the first medical image 102 can be a current-year mammographic view of a breast, while the second medical image 104 can be a prior-year mammographic view of that breast. Alternatively, the first medical image 102 can be a current-year mammographic view of the left breast, while the second medical image 104 can be a current-year mammographic view of the right breast, in which case one or the other image has been laterally flipped as part of the spatial registration process. A variety of different combinations of temporal comparison and bilateral comparison are advantageously facilitated in accordance with one or more of the preferred embodiments. More generally, the medical images 102 and 104 can be from any medical imaging modality such as, but not limited to, x-ray, ultrasound, CT, MRI, PET, SPECT, etc. Alternatively, the medical images 102 and 104 can be from different ones of the above medical imaging modalities acquired at the same time or at different times, or can be from parallel planes of a three-dimensional data volume, or from parallel planes of a quasi-three-dimensional volume such as an x-ray tomosynthesis result set. A variety of different combinations of multi-modality comparison, temporal comparison, bilateral comparison, and nearby-plane comparison are advantageously facilitated in accordance with one or more of the preferred embodiments.

According to a preferred embodiment, the first and second medical images 102 and 104 are displayed on a softcopy review workstation monitor 106 such that the second medical image 104 appears as a spatially registered underlay to the first medical image 102 exposed through an aperture 108 therein. The aperture 108 comprises an edge 110 that is viewer-manipulable in a back-and-forth manner, as indicated by the arrows 112 in FIG. 1. This provides for visual comparison of the first and second medical images 102 and 104 with minimal eye movement as compared to a full side-by-side display thereof.

The amount or degree of spatial registration between the medical images 102 and 104 can vary widely across a broad range of possibilities without departing from the scope of the present teachings. For example, in one preferred embodiment, the spatial registration can be very rough, perhaps being achieved only by ensuring that the medical images are at the same spatial scale. In another preferred embodiment, the spatial registration can be very precise, as may be achieved by combinations of affine transformation and image warping. In still another preferred embodiment, the medical images can be placed in both grayscale registration and spatial registration, as described, for example, in U.S. 2005/0163360 A1, which is incorporated by reference herein. As used herein, spatial registration includes any lateral flipping necessary to bring laterally corresponding medical images, such as those of the left breast and right breast or of the left lung and right lung, into spatial correspondence.

Viewer manipulation of the edge 110 in a back-and-forth manner can be achieved using any of a variety of known methods, such as cursor click-and-drag, turning of a specialized knob, and so on. The viewer manipulation of the edge 110 can also be semi-automated, such as by selecting the edge 110 and instantiating a cine-type display of the moving edge 110. Although illustrated as a rectangle in FIG. 1, the aperture 108 can have any of a variety of geometric shapes, and it is not required that the edge 110 be a straight line. The back-and-forth movement of the manipulated edge of the aperture can be in any desired direction, e.g., top-to-bottom, left-to-right, or any oblique angle. Also, more than one edge of the aperture can be movable. In one preferred embodiment, all of the edges of the aperture move in unison, the aperture thereby appearing fixed in size and shape while slidably translating across the screen.

Among other advantages provided by one or more of the preferred embodiments, the displayed portions of the medical images 102 and 104 are not required to be mutually synthesized (e.g., by difference imaging, fusion, etc.) and therefore can look more like "original" or "diagnostic-quality" medical images with which radiologists are more comfortable and experienced. At the same time, viewer eye movement is advantageously minimized as compared to general side-by-side placement of the medical images. It is to be appreciated, however, that the scope of the preferred embodiments is not necessarily limited to scenarios in which the medical images look like "original" or "diagnostic-quality" images. In other preferred embodiments, one or both of the medical images 102 and 104 can themselves be processed versions of the originals such as, but not limited to, CAD-highlighted versions, grayscale or color-enhanced versions, filtered versions, difference-enhanced versions, fused versions, and so on. By way of example, the first medical image 102 could be a difference image of two original source images, and the second medical image 104 could be a sum of two original source images. As another example, the first and second medical images can be locally processed near the lateral boundary therebetween (i.e., near the edges of the aperture 108) in a manner that emphasizes the image differences, such as by high-pass filtering, grayscale ramping, color ramping, etc.

Figure 2D:
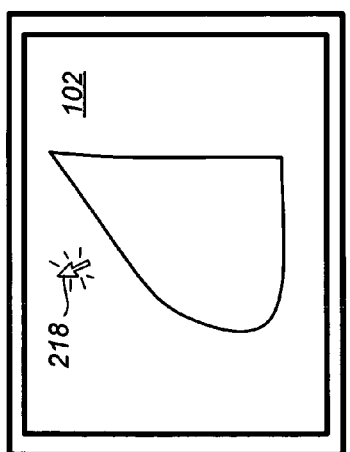
FIGS. 2A-2F illustrate a review workstation display facilitating comparison of two medical images according to a preferred embodiment.
Figure 2E:
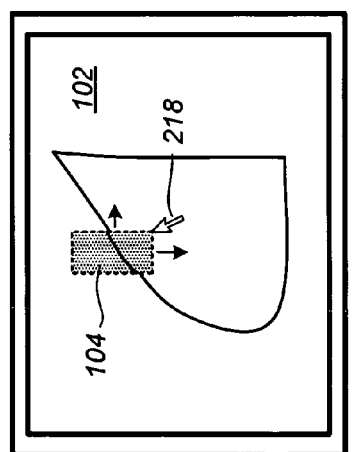
Figure 2F:
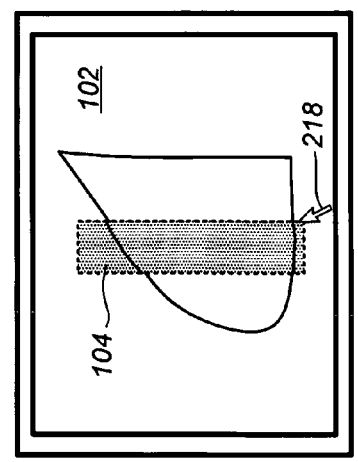
Figure 2A:
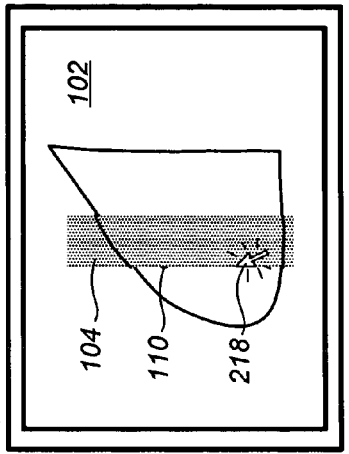
Figure 2B:
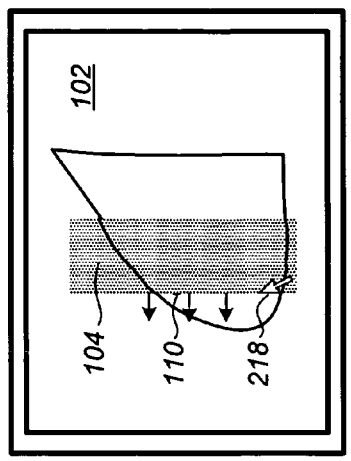
Figure 2C:
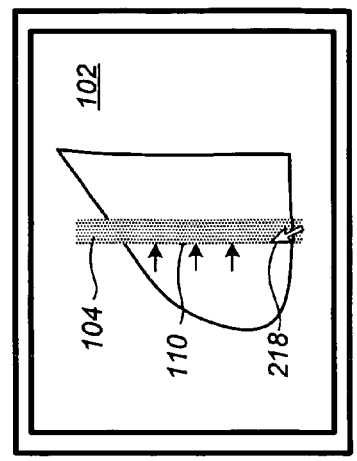

FIGS. 2A-2F illustrate one of the many ways in which the viewer may form and manipulate the aperture 108 of FIG. 1. In this example, the viewer starts by viewing only the first medical image 102. The viewer then clicks their cursor 218 at a starting point (FIG. 2A), and then drags the cursor 218 to an end point to form the aperture through which the second image 104 is visible (FIGS. 2B-2C). The viewer can click on the edge 110 (FIG. 2D) and then drag it back and forth as desired (FIGS. 2E-2F), the second image 104 being openably and closeably exposed.

Preferably, the edge 110 is a "hard" edge, i.e., it is a zero-pixel transition region between the first and second medical images. To explain further, letting $I1(x,y)$ and $I2(x,y)$ represent the (spatially registered) matrices for the first and second medical images, and letting the edge 110 be vertically oriented along a column at an abscissa pixel $x_{edge}$, then a typical row at an ordinate $y_0$ in the vicinity of the edge 110 would have pixel values of [ . . . , $I1(x_{edge}-2,y_0)$, $I1(x_{edge}-1,y_0)$, $I1(x_{edge},y_0)$, $I2(x_{edge}+1,y_0)$, $I2(x_{edge}+2,y_0)$, . . . ]. Using such "hard" edge between the first and second medical images can result in a visually apparent edge even when differences between the first and second medical images are relatively slight in that vicinity, while also preserving the "originality" of both of the medical images in that vicinity. In other preferred embodiments, a visible line (e.g., black, white, bright-colored) can be provided at the edge to provide demarcation between the first and second medical images.

FIG. 3 illustrates a review workstation display 306 for facilitating comparison of first and second medical images 302 and 304 according to a preferred embodiment. A first aperture 308 in the first medical image 302 through which the second image 304 appears occupies an entire left hemi-plane of the first medical image 302, with only a single viewer-manipulable edge 320 appearing between the images. Also shown in FIG. 3 is a legend icon 324 straddling the edge 320, the legend icon 324 automatically sliding back and forth with the edge 320. The legend icon 324 comprises textual identifiers 326 that remindably communicate the salient clinical difference(s) between the displayed images as the edge 320 is moved back and forth. In this particular case, the textual identifiers 326 remindably indicate the acquisition dates of the mammographic images being temporally compared.

FIG. 4 illustrates the review workstation monitor 306 for facilitating comparison of a third medical image 402 in conjunction with the first and second medical images 302 and 304 according to a preferred embodiment. More particularly, the third medical image 402 is displayed such it appears as a spatially registered underlay to the second medical image 304 exposed through a second aperture 408 therein. The third medical image 402 will only be viewable, of course, when the second aperture 408 is at least partially viewable through the first aperture 308 in the first medical image. The second aperture 408 also comprises an edge 420 that is viewer-manipulable in a back-and-forth manner so that the three medical images 302, 304, and 402 can be visually compared with minimal eye movement.

Figure 5:
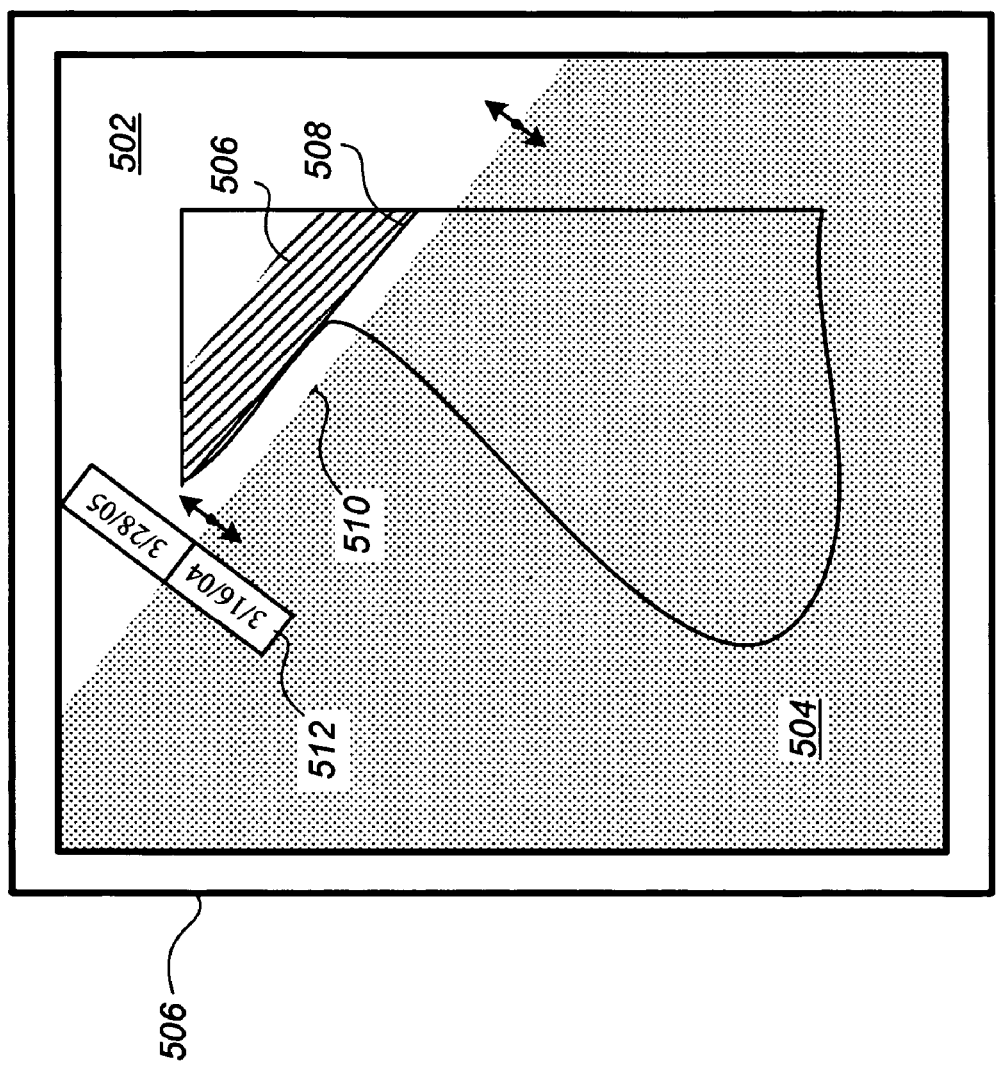
FIG. 5 illustrates a review workstation display facilitating comparison of two medical images according to a preferred embodiment.

FIG. 5 illustrates a review workstation display facilitating comparison of first and second medical images 502 and 504 according to a preferred embodiment, for the particular case in which both medical images are MLO or LAT views of (a) a single breast for the case of temporal comparison, or (b) the left and right breasts for bilateral comparison. For these views, a pectoral muscle 506 appears relatively prominently and a boundary 508 thereof is also usually prominent. According to this embodiment, an aperture edge 510 forming a lateral boundary between the first and second medical images 502 and 504 is substantially straight and substantially parallel to the pectoral muscle boundary 508. Manipulation of the edge 510 at least partially mimics one known advantageous method for reviewing and/or comparing film-based MLO/LAT mammograms. Also shown in FIG. 5 is a legend icon 512 automatically sliding back and forth with the edge 510.

Figure 6:
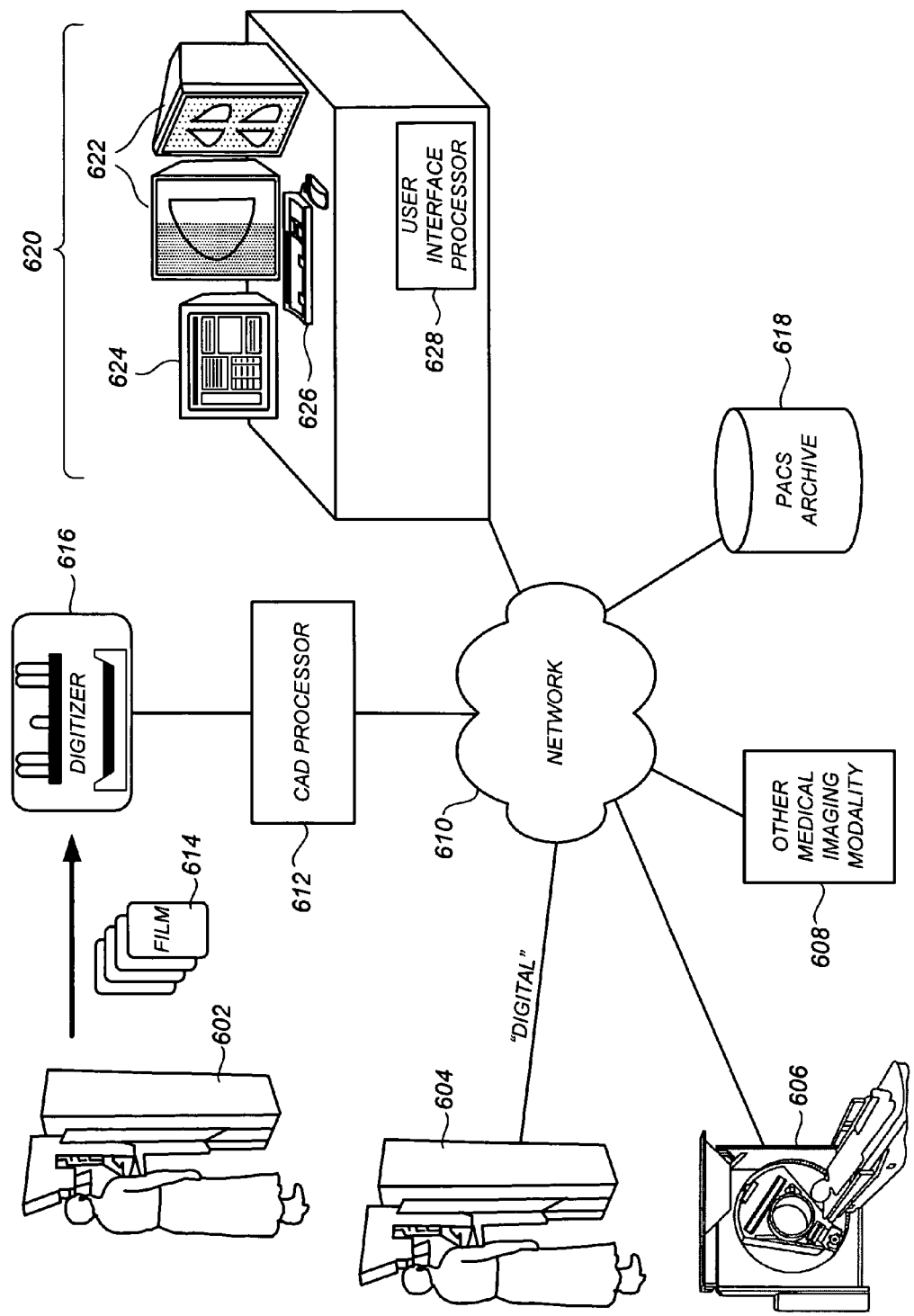
FIG. 6 a conceptual diagram of a medical imaging environment for which one or more of the preferred embodiments is particularly advantageous.

FIG. 6 illustrates a conceptual diagram of a medical imaging environment for which one or more of the preferred embodiments is particularly suited. Shown in FIG. 6 is a network 610, which may be a HIS/RIS (Hospital Information System/Radiology Information System) network, to which is coupled a film mammogram acquisition device 602, a digital mammogram acquisition device 604, a computed tomography (CT) acquisition device 606, and a generalized "other" medical imaging device 608. A computer-aided detection (CAD) processor 612 coupled to the network 610 receives digital medical images from one or more of the devices 604-608, and/or from a digitizer 616 that digitizes x-ray mammogram films 614 generated by the film mammogram acquisition device 602. The CAD processor 612 processes the medical images according to a CAD processing algorithm. It is to be appreciated, however, that the preferred embodiments can also be advantageously applied in medical imaging environments not having CAD capabilities, in which case the CAD processor 612 is not present. The medical images are then viewed (in conjunction with the associated CAD results, if present) at a radiology review workstation 620.

Preferably, the various medical images and related information are communicated according to the DICOM (Digital Imaging and Communications in Medicine) standard and the network 610 supports the TCP/IP protocol, which is used as the transport protocol for the DICOM standard. Also coupled to the network 610 is a PACS (Picture Archiving and Communication System) archive 618, generally representing a repository for medical information associated with the medical imaging environment, including both current and archived images, current and archived CAD results (if present), radiology reports for completed cases, and so forth.

Although one or more of the preferred embodiments is particularly advantageous when used in an x-ray mammography environment having CAD processing capabilities, it is to be appreciated that the preferred embodiments can also be advantageously applied using other medical imaging modalities and/or in medical imaging environments not having CAD capabilities. As indicated by the presence of the CT acquisition device 606 and the "other" medical imaging device 608 in FIG. 6, the preferred embodiments described herein are readily applicable for a variety of present or prospective non-mammography medical imaging modalities such as CT, MRI, PET, SPECT, ultrasound, x-ray tomosynthesis, thermography, electrical conductivity-based modalities, and other modalities.

In one preferred embodiment, the review workstation 620 comprises a multi-modality workstation adapted and configured for a mammography environment. In one example, a Sectra IDS5/mx.net dedicated mammography workstation can be used that allows for third-party plug-ins. Review workstation 620 comprises a diagnostic display 622, an administrative display 624, user input devices 626 (e.g., keyboard, mouse, trackball, pointers, etc), and a user interface processor 628. Administrative display 624 is used for input and output of a wide variety of information that may be associated with a particular set of medical images (e.g., listings, tables, plots, text descriptions, etc), as well as for system installation, maintenance, updating, and related tasks.

Notably, the medical imaging environment of FIG. 6 is presented by way of example only and is not intended to limit the scope of the preferred embodiments to this particular scenario. By way of example, different combinations of the devices of FIG. 6 can be placed adjacently to each other or integrated into the same hardware boxes without departing from the scope of the preferred embodiments. By way of still further example, the network 610 can be a wide-area network with the different nodes being distributed throughout a city, a country, or the world. Alternatively, and by way of still further example, some or all of the transfer of digital information can be achieved by physical transfer of disks, memory sticks, or other digital media devices without departing from the scope of the preferred embodiments. In view of the present disclosure, a person skilled in the art would be able to construct such plug-ins or other software packages capable of achieving the described user interfaces and processing functionalities without undue experimentation, using publicly available programming tools and software development platforms.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, a softcopy review workstation providing for medical image comparison according to one or more of the preferred embodiments supra may also incorporate one or more methods from U.S. 2004/0122787 A1, supra, in a combined and/or adjunctive sense, without departing from the scope of the present teachings. Therefore, reference to the details of the preferred embodiments are not intended to limit their scope, which is limited only by the scope of the claims set forth below.

What is claimed is:

1. A method for facilitating viewer comparison of a plurality of medical images of at least one body part on a softcopy review workstation, the softcopy review workstation including at least one processor and a display device, the method being implemented by the softcopy review workstation, the method comprising:
    receiving, by the softcopy review workstation, first and second medical images of the at least one body part; and
    displaying, by the softcopy review workstation, said first and second medical images on said display device such that the second medical image appears as a spatially registered underlay to the first medical image exposed through a first aperture therein, the first medical image masking the second medical image outside the first aperture, the second medical image masking the first medical image inside the first aperture, said first aperture having at least one edge that is viewer-manipulable in a back-and-forth manner so that the first and second medical images can be visually compared with minimal eye movement.

2. The method of claim 1, wherein said first aperture comprises one of (i) an entire half-plane of the first medical image such that said at least one edge consists of a single line thereacross, and (ii) a viewer-definable geometric shape including said at least one edge that openably and closeably exposes the second medical image from underneath the first medical image according to viewer manipulations of said at least one edge.

3. The method of claim 1, wherein said first and second medical images comprise (i) identical views of a same body part acquired at different times using a same medical imaging modality, or (ii) corresponding views of laterally corresponding body parts acquired using the same medical imaging modality, wherein said medical imaging modality is selected from the group consisting of: x-ray, ultrasound, computerized tomography (CT), magnetic resonance imaging (MRI), positron emission tomography (PET), and single-photon emission computed tomography (SPECT).

4. The method of claim 1, wherein said first and second medical images are acquired substantially concurrently using different medical imaging modalities selected from the group consisting of: x-ray, ultrasound, computerized tomography (CT), magnetic resonance imaging (MRI), positron emission tomography (PET), and single-photon emission computed tomography (SPECT).

5. The method of claim 1, wherein said first and second medical images are derived from nearby parallel planes of a common data volume acquired using a three-dimensional imaging modality.

6. The method of claim 1, wherein said first and second medical images represent nearby parallel planes of a breast volume acquired from an x-ray tomosynthesis modality.

7. The method of claim 1, wherein said at least one edge is sufficiently sharp such that a lateral boundary between the first and second medical images corresponding to said at least one edge is visually apparent even when differences between the first and second medical images are relatively slight in a vicinity of said at least one edge.

8. The method of claim 7, further comprising processing said first and second medical images near said at least one edge to provide visual emphasis of said lateral boundary.

9. The method of claim 8, wherein said processing comprises one of more of high-pass spatial filtering, grayscale ramping, colorization, and image warping.

10. A softcopy review workstation, comprising:
    a display device;
    a user input device; and
    a processor in communication with said display device and said user input device, said processor causing said display device to display a first medical image and a second medical image of at least one body part such that the second medical image appears as a spatially registered underlay to the first medical image exposed through a first aperture therein, the first medical image masking the second medical image outside the first aperture, the second medical image masking the first medical image inside the first aperture, said first aperture having at least one edge that is movable by actuation of said user input device, whereby the first and second medical images can be visually compared with minimal user eye movement.

11. The softcopy review workstation of claim 10, wherein said first aperture comprises one of (i) an entire half-plane of the first medical image such that said at least one edge consists of a single line thereacross, and (ii) a user-definable geometric shape including said at least one edge that openably and closeably exposes the second medical image from underneath the first medical image according to said actuation of said user input device.

12. The softcopy review workstation of claim 10, wherein said first and second medical images comprise (i) identical views of a same body part acquired at different times using a same medical imaging modality, or (ii) corresponding views of laterally corresponding body parts acquired using the same medical imaging modality, wherein said medical imaging modality is selected from the group consisting of: x-ray, ultrasound, computerized tomography (CT), magnetic resonance imaging (MRI), positron emission tomography (PET), and single-photon emission computed tomography (SPECT).

13. The softcopy review workstation of claim 10, wherein said first and second medical images are acquired substantially concurrently using different medical imaging modalities selected from the group consisting of: x-ray, ultrasound, computerized tomography (CT), magnetic resonance imaging (MRI), positron emission tomography (PET), and single-photon emission computed tomography (SPECT).

14. The softcopy review workstation of claim 10, wherein said first and second medical images are derived from nearby parallel planes of a common data volume acquired using a three-dimensional imaging modality.

15. The softcopy review workstation of claim 10, wherein said first and second medical images represent nearby parallel planes of a breast volume acquired from an x-ray tomosynthesis modality.

16. The softcopy review workstation of claim 10, wherein said at least one edge is sufficiently sharp such that a lateral boundary between the first and second medical images corresponding to said at least one edge is visually apparent even when differences between the first and second medical images are relatively slight in a vicinity of said at least one edge.

17. A computer readable medium tangibly embodying one or more sequences of instructions wherein execution of the one or more sequences of instructions by one or more processors causes the one or more processors to facilitate viewer comparison of a plurality of medical images of at least one body part, comprising:

displaying said first and second medical images of said at least one body part such that the second medical image appears as a spatially registered underlay to the first medical image exposed through a first aperture therein, the first medical image masking the second medical image outside the first aperture, the second medical image masking the first medical image inside the first aperture; and slidably translating at least one edge of said first aperture responsive to at least one viewer input so that the first and second medical images can be visually compared with minimal eye movement.

18. The computer readable medium of claim 17, wherein said first aperture comprises one of (i) an entire half-plane of the first medical image such that said at least one edge consists of a single line thereacross, and (ii) a viewer-definable geometric shape including said at least one edge that openably and closeably exposes the second medical image from underneath the first medical image according to said slidable translation of said at least one edge.

19. The computer readable medium of claim 17, wherein said first and second medical images comprise (i) identical views of a same body part acquired at different times using a same medical imaging modality, or (ii) corresponding views of laterally corresponding body parts acquired using the same medical imaging modality, wherein said medical imaging modality is selected from the group consisting of: x-ray, ultrasound, computerized tomography (CT), magnetic resonance imaging (MRI), positron emission tomography (PET), and single-photon emission computed tomography (SPECT).

20. The computer readable medium of claim 17, wherein said first and second medical images are acquired substantially concurrently using different medical imaging modalities selected from the group consisting of: x-ray, ultrasound, computerized tomography (CT), magnetic resonance imaging (MRI), positron emission tomography (PET), and single-photon emission computed tomography (SPECT).

21. The computer readable medium of claim 17, wherein said first and second medical images represent nearby parallel planes of a breast volume acquired from an x-ray tomosynthesis modality.

22. The computer readable medium of claim 17, wherein said first and second medical images are derived from nearby parallel planes of a common data volume acquired using a three-dimensional imaging modality.

23. The computer readable medium of claim 17, wherein said at least one edge is sufficiently sharp such that a lateral boundary between the first and second medical images corresponding to said at least one edge is visually apparent even when differences between the first and second medical images are relatively slight in a vicinity of said at least one edge.

* * * * *